United States Patent [19]
Fevig et al.

[11] Patent Number: 6,037,478
[45] Date of Patent: Mar. 14, 2000

[54] SYNTHESIS OF 3-CARBOMETHOXY-4,5-DIMETHYLTHIOPHENE

[75] Inventors: Thomas L. Fevig, Wildwood; Patrick H. Lau, Chesterfield; Wendell G. Phillips, Wildwood, all of Mo.

[73] Assignee: Monsanto Company, St. Louis, Mo.

[21] Appl. No.: 09/394,760

[22] Filed: Sep. 13, 1999

Related U.S. Application Data

[63] Continuation of application No. 09/170,441, Oct. 13, 1998
[60] Provisional application No. 60/061,972, Oct. 14, 1997.

[51] Int. Cl.$^7$ .................................................. C07D 333/26
[52] U.S. Cl. ..................................................... 549/4
[58] Field of Search ................................................... 549/4

[56] References Cited

U.S. PATENT DOCUMENTS

| | | | |
|---|---|---|---|
| 4,041,047 | 8/1977 | Vlattas | 260/332.1 |
| 4,689,343 | 8/1987 | Gayer et al. | 514/445 |
| 5,034,049 | 7/1991 | Kober et al. | 71/90 |
| 5,073,184 | 12/1991 | Anthony et al. | 71/90 |
| 5,087,288 | 2/1992 | Welter | 71/90 |
| 5,206,375 | 4/1993 | Schefczik et al. | 548/152 |
| 5,403,939 | 4/1995 | Yazawa et al. | 549/57 |
| 5,486,621 | 1/1996 | Phillion et al. | 549/4 |
| 5,498,630 | 3/1996 | Phillion et al. | 514/443 |
| 5,679,801 | 10/1997 | Caufield et al. | 549/61 |
| 5,747,518 | 5/1998 | Yoshikawa et al. | 514/403 |

FOREIGN PATENT DOCUMENTS 32 29 538 A1  2/1984  Germany.

OTHER PUBLICATIONS

Asinger, Friedrick, et al., "Joint Reaction of Sulfur And Ammonia With Methyl Ethyl Ketone," Liebigs Ann. Chem., Bd. 610, pp. 25–32 (1957).

Coppola, Gary M., et al., "Synthesis Of Highly Functionalized Thiophenes, 4–Aryl–3–Carboxylate Derivatives," Synlett, p. 1143 (Nov. 1995).

Dubief, Roland, et al., "A Study of Δ–Thiazolines As Antiradiation Agents," Eur. J. Med. Chem.—Chim. Ther., No. 6, pp. 461–466 (1986).

Hoffmann, Reinhard W., et al., "The Sense Of Asymmetric Induction On Addition To α–Chiral Aldehydes," Chem. Ber., vol. 118, pp. 3966–3979 (1985).

Chemical Abstract No. 70433h, vol. 71, No. 15 (Oct. 13, 1969).

Chemical Abstract No. 94:103096f, vol. 94, No. 13 (Mar. 30, 1981).

*Primary Examiner*—Deborah C. Lambkin
*Attorney, Agent, or Firm*—Thomas P. McBride; Arnold White & Durkee

[57] ABSTRACT

Fungicides having thiophene rings may be made from the intermediate compound 3-carbomethoxy-4,5-dimethylthiophene. That compound, and related compounds, may be produced by reacting an alpha mercaptoketone, e.g., 3-mercapto-2-butanone, with an acrylate, e.g., methyl-3-methoxy acrylate, in the presence of an alkoxide base, e.g., NaOMe, to form the substituted tetrahydrothiophene, followed by conversion to the aromatic thiophene with an acid treatment. The substituted tetrahydrothiophene is a novel compound.

8 Claims, No Drawings

SYNTHESIS OF 3-CARBOMETHOXY-4,5-DIMETHYLTHIOPHENE

This application is a continuation of U.S. Application Ser. No. 09/170,441, filed Oct. 13, 1998, now allowed, which is based on U.S. Provisional Application No. 60/061,972, filed Oct. 14, 1997.

BACKGROUND OF THE INVENTION

This invention relates generally to the synthesis of substituted thiophenes and, more particularly, to 3-carbomethoxy-4,5-dimethylthiophene, which is an intermediate to a family of fungicides. In another aspect, the invention relates to a novel compound, which is a precursor of the thiophene intermediates.

One fungicide that may be made from the subject intermediate is 4,5-dimethyl-N-2-propenyl-2-(trimethylsilyl)-3-thiophenecarboxamide, which is claimed as a novel compound in U.S. Pat. No. 5,486,621. Two methods of making such a compound are provided therein. Another method is described in U.S. Pat. No. 5,498,630, which concerns more generally controlling Take-All disease of plants by applying a fungicide. One related thiophene fungicide is described in Example 271, along with the method of making such compound.

A number of methods of making thiophene compounds have been disclosed. One method that is related to the method of the present invention is described, for example, in SYNLETT, Nov. 1995, p. 1143, by G. M. Coppola, R. E. Damon, and H. Yu. That method reacts an alpha-mercaptoketone with a phosphorus-substituted acrylate in the presence of a base to form a substituted dihydrothiophene ring, from which the corresponding aromatic thiophene ring can be made. It has been believed that the presence of a phosphorus-containing moiety at the 2-position was necessary for the cycloaddition reaction to occur. It has been found that it is not required, but when the 3-position is substituted, the reaction is possible in the presence of certain bases. The new method may be applied to produce thiophene rings having various substituents, including those of the titled compound, as will be seen in the description below.

SUMMARY OF THE INVENTION

In one aspect, the invention is a new method of forming substituted thiophene rings and derivatives, such as the fungicide of U.S. Pat. No. 5,486,621. The new method reacts an alpha mercaptoketone, such as 3-mercapto-2-butanone, prepared in situ from an α-haloketone such as 3-chloro-2-butanone, with an acrylate, such as methyl-3-methoxyacrylate, in the presence of an alkoxide base, such as NaOMe, when dissolved in an aprotic solvent, e.g., toluene. The product of the reaction is a substituted tetrahydrothiophene, which can be converted to the aromatic thiophene by an acid treatment. The generic reaction can be written as follows:

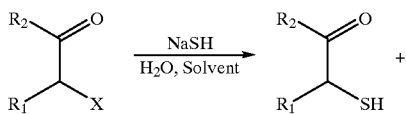

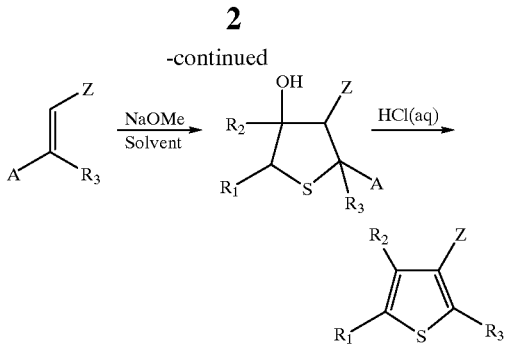

where: $R_1$ and $R_2$ are independently chosen from hydrogen, alkyl, aryl, the substituted equivalents thereof, and a ring formed from $R_1$ and $R_2$ having 5 to 7 atoms; X is a suitable leaving group such as halogen (Cl, Br, I) or methanesulfonyloxy; $R_3$ is a member of the group of hydrogen, alkyl, aryl, and the substituted equivalents thereof; Z is CN or $CO_2R_4$, wherein $R_4$ is chosen from the group consisting of alkyl and aryl and the substituted equivalents thereof, H, Na, Li, K, and $NH_4^+$; and A is an alkoxy group, preferably a $C_1$–$C_6$ straight or branched alkoxy group.

In another aspect, the invention is a method of making the fungicide 4,5-dimethyl-N-2-propenyl-2-(trimethylsilyl)-3-thiophenecarboxamide and related compounds in which the propenyl group is replaced by $C_2$ to $C_4$ branched or straight alkyl chain.

In still another aspect, the invention is the precursor compound of the thiophene intermediate, as illustrated in the schematic diagram of the reaction shown above.

DESCRIPTION OF ILLUSTRATIVE EMBODIMENTS

Mercaptoketones

The sulfur atom in the substituted thiophene compound is supplied by a mercaptoketone having the formula

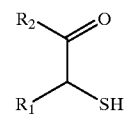

where $R_1$ and $R_2$ are defined above.

The preferred compounds will be determined by the substitutions that one desires for the thiophene in the 4- and 5-positions. In turn, these may be the substitutions desired in a fungicide or other compound for which the thiophene is an intermediate. Alternatively, $R_1$ and $R_2$ could be selected to facilitate their replacements by substituents that are desired in the ultimate chemical product.

In a preferred embodiment, $R_1$ and $R_2$ are methyl. Examples of other mercaptoketones include, but are not limited to,

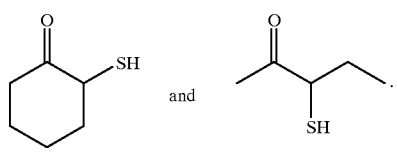

Mercaptoketones such as those used in the present invention are known in the literature. They are typically prepared by treating the corresponding haloketones (Eur. J. Med. Chem.—Chim. Ther. 1986-21, No. 6, p. 461 by R. Dubief, Y. Robbe, J.-P. Fernandez, G. Subra, A. Terol, J.-P. Chapat, H. Sentenac-Roumanou, and M. Fatome) in solvents with NaSH or other sulfur sources, or from the ketones by treatment with ammonia and elemental sulfur (Liebigs Ann. Chem. 1957, Bd. 610, p. 25 by F. Asinger, M. Thiel, and I. Kalzendorf). In some cases, such as with 3-mercapto-2-butanone, isolated yields of the mercaptans are low due to degradation of the products during purification. For the purpose of the present invention, it has been found that mercaptoketones, such as with 3-mercapto-2-butanone, can be prepared from α-haloketones, such as 3-chloro-2-butanone, in a two-phase solvent system comprising water and a nonpolar organic solvent such as toluene or heptane, in the presence of NaSH. The product mercaptoketone is then recovered in high yield and purity as a solution in the organic solvent after phase separation, thereby avoiding the degradation associated with purification. Water can be removed from the mercaptoketone solution by various means such as by azeotropic distillation or by bringing the solution in contact with desiccants such as molecular sieves, calcium chloride, or sodium sulfate, prior to reaction with the acrylic compound.

Acrylates

The second compound that adds to the mercaptoketone to make the substituted thiophene is an acrylic compound defined by the formula

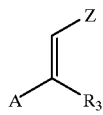

where $R_3$ and Z are as defined above, A is selected from the group consisting of alkoxy.

It has been thought that a phosphorus-containing moiety was needed in the 2-position to cause the thiophene ring to be formed. It has been found, however, that the reaction can be carried out with good yields of the thiophene ring when a moiety A is in the 3-position and an effective base is used as a catalyst. Examples of reactive moieties A are alkoxy.

In a preferred embodiment, A is methoxy. Examples of the reactive acrylic compound include, but are not limited to,

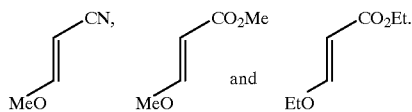

Tetrahydrothiophene Precursor

The reaction product of the mercaptoketone and acrylic compound just described is the substituted thiophene

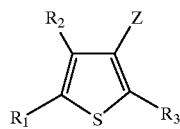

where $R_1$, $R_2$, $R_3$, and Z are described above.

Under certain conditions, the product, in whole or in part, may be the corresponding tetrahydrothiophene, that is,

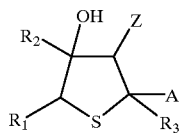

including all of the stereoisomers thereof. This is believed to be a novel compound. It may be converted to the thiophene by reaction with an acid, as will be seen in the discussion below.

Reaction Conditions

The reaction of an α-haloketone with NaSH is carried out in a two-phase, water/organic solvent system. Thus a solution of 1–1.25 equivalents of NaSH in water (10–30 wt %) is prepared and combined with an organic solvent such as toluene or heptane (2–4 equivalents) under an inert atmosphere with vigorous stirring. The mixture is maintained between about 0° C. and about 30° C. as the α-haloketone is added. When the reaction is complete (0.5–4 h), the phases are allowed to separate, and the lower, aqueous phase is discarded. The upper, organic phase is then dried by azeotropic distillation (30–50° C., 100–600 mmHg) or by contact with a desiccant such as molecular sieves, calcium chloride, or sodium sulfate for a sufficient amount of time (15 min to 3 h).

The reaction of the mercaptoketone and acrylic compound is carried out in the presence of a base catalyst. Examples of base catalysts are alkoxides such as sodium methoxide, sodium t-amylate, potassium t-amylate, and potassium t-butoxide; strong amine bases such as diazabicycloundecene; sodium hydride; and alkali metal hydroxides. The base is preferably an alkoxide. Generally, the amount of the base catalyst will be about 0.025–0.2 equivalents relative to the amount of the mercaptoketone. Larger amounts of the base catalyst have been found to yield the thiophene, although the yields are lower. The product under the preferred conditions comprises a substantial proportion of tetrahydrothiophene.

Although it is not considered to be essential, the reaction will be carried out while the reactants are dissolved in a solvent, preferably, a hydrocarbon solvent such as toluene or another aprotic solvent such as chlorobenzene, heptane, or xylene.

The reaction may be carried out at temperatures in the range of about 0–50° C. The treatment of the reaction product with acid to convert any tetrahydrothiophene to the thiophene form is preferably carried out at about 0–50° C.

Recovery of the substituted thiophene from the reaction mixture may be carried out in at least two ways. In the first, the tetrahydrothiophene is recovered by separating it from the reaction mixture and then reacting it with acid to convert it to the thiophene. The second method reacts the tetrahydrothiophene in-situ with acid and subsequently recovers the product in the thiophene form.

The first recovery process will include at least the following steps. Dilute sulfuric acid will be added to the reaction mixture in order to neutralize the reaction mixture. Then, a solvent, such as ethyl acetate, will be added, and water and organic phases will be separated. The organic phase, which includes the reaction product, will be washed with aqueous brine. After this, the washed organic phase will be dried, for example, by contact with sodium sulfate and the solvent evaporated to yield a mixture of substituted tetrahydrothiophene and substituted thiophene. This mixture will be treated with an aqueous acid, such as concentrated HCl, 50% $H_2SO_4$, or 50% phosphoric acid, or a non-aqueous acid such as anhydrous methanesulfonic acid, to convert the tetrahydrothiophene to the thiophene form. After that reaction, the steps described above can be repeated to separate the thiophene product.

In the second method, the substituted tetrahydrothiophene is converted in-situ to the thiophene form rather than being first separated. First, an aqueous acid, such as concentrated HCl or 50% $H_2SO_4$, will be added to the reaction mixture to convert the tetrahydrothiophene to the thiophene form. Then, the water and organic phases will be separated and the solvent evaporated. Finally, the crude product may be distilled to produce the refined substituted thiophene.

Thiophene Intermediate

The product of the invention is a substituted thiophene, which is an intermediate for preparation of a family of thiophene-based fungicides described in U.S. Pat. No. 5,498,630 and, in particular, 4,5-dimethyl-N-2-propenyl-2-(trimethylsilyl)-3-thiophene carboxamide disclosed and claimed in U.S. Pat. No. 5,486,621. The entirety of each of U.S. Pat. Nos. 5,498,630 and 5,486,621 are hereby incorporated by reference. Such fungicides are useful for control of Take-All disease in plants, caused by the soil-borne fungus *Gaeumannomyces graminis*. This fungus infects the roots of certain plants, particularly cereal grains such as wheat and barley.

The thiophene intermediate is defined by the formula

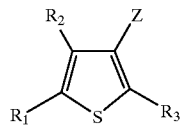

where the substituents $R_1$, $R_2$, $R_3$, and Z are as defined above.

In the preferred fungicide, $R_1$ and $R_2$ are methyl, $R_3$ is trimethylsilyl ($SiMe_3$), and Z is $CONH—CH_2CH=CH_2$. This generally requires that $R_3$, which is preferably hydrogen in the acrylic starting compound, must be replaced by the trimethylsilyl moiety or another desired substituent. This can be achieved by treating the thiophene intermediate above, wherein Z is $CO_2Li$, with a strong base followed by treatment with trimethylsilyl chloride. Typically, Z will be a carboxylic acid ester moiety. Therefore, hydrolysis of the carboxylic acid ester moiety to the corresponding Li salt followed by silylation as described above and subsequent conversion to the amide by standard methods would give the preferred fungicide.

EXAMPLE 1

Aqueous NaSH (1.1 equivalents) was diluted with water to give a 23.5% solution by weight. This solution was combined with 3 equivalents of toluene under an inert atmosphere, stirred vigorously, and cooled to 5° C. One equivalent of 3-chloro-2-butanone was added to the mixture at a rate to keep the temperature below 10° C. This required 2 h. After the addition, the mixture was stirred at 5–10° C. until GC analysis of the mixture showed complete consumption of the chlorobutanone (15 min to 1 h). Stirring was stopped, and the phases were allowed to separate. After standing for 15 min, the aqueous phase was drained out and treated with bleach to oxidize and deodorize sulfur compounds. The upper, organic phase containing about 25% by weight of 3-mercapto-2-butanone was dried over activated 4A molecular sieves (about 35 g/kg of solution) for 1 h. The solution of 3-mercapto-2-butanone was then decanted from the sieves into a reaction vessel for the next step.

EXAMPLE 2

The toluene solution of 3-mercapto-2-butanone from the previous step (613 g of ca. 25 wt % solution) was placed in a clean, dry reactor along with 15 g of methyl-3-methoxyacrylate. The mixture was warmed to 25° C., stirred vigorously, and treated with solid sodium methoxide (8.5 g, ca. 0.1 equiv.) all at once. The remaining methyl-3-methoxyacrylate (151 g) was added in at a rate to keep the temperature at or below 35° C. (2 h). The resulting mixture was allowed to reach room temperature and stir for 21 h. Concentrated hydrochloric acid (88 g) was added to the mixture over 30 min such that the temperature did not exceed 35° C. The resulting mixture was stirred vigorously for 2 h, then treated with 73 g of water, and stirred for 10 min more. The phases were allowed to separate. After standing for 10 min, the aqueous phase was drained from the reactor, and the upper, product phase was washed with 100 g of 5% sodium bicarbonate solution. After being stirred for 15 min, the phases were allowed to separate. The lower, aqueous phase was drained from the reactor, and the upper, product phase was transferred to a distilling flask. The toluene was distilled through a 5-plate distillation column at 100 mmHg. After a small fraction containing toluene and other low boiling impurities was collected, the product, 3-carbomethoxy-4,5-dimethylthiophene, was distilled through the column at 50 mmHg. A total of 202.4 g of product was collected with a purity of 98.8% by weight % analysis. This corresponds to a yield of 77% from 3-chloro-2-butanone, and 82% from methyl-3-methoxyacrylate.

EXAMPLE 3

One equivalent of each of 3-mercapto-2-butanone and methyl-3-methoxyacrylate were dissolved in toluene, and 0.1 equivalent of NaOMe was added as a catalyst. The reaction was carried out at room temperature under a nitrogen atmosphere for 3–4 hours. Then, the mixture was poured into dilute sulfuric acid and extracted with ethyl acetate. The organic phase was washed with brine and then dried over sodium sulfate, filtered and evaporated. The product was the tetrahydrothiophene precursor described above, i.e., 2-methoxy-3-carbomethoxy-4-hydroxy-4'-methyl-5-methyl-tetrahydrothiophene.

The tetrahydrothiophene precursor was treated with concentrated HCl at room temperature with rapid stirring. After 5 minutes, the mixture was poured into water and extracted with ethyl acetate. The organic phase was washed with saturated $NaHCO_3$, dried over $NaSO_4$, filtered and evaporated at room temperature on a rotary evaporator, leaving the aromatic thiophene product, 3-carbomethoxy-4,5-dimethylthiophene.

What is claimed is:

1. A process for making a substituted thiophene compound having the formula

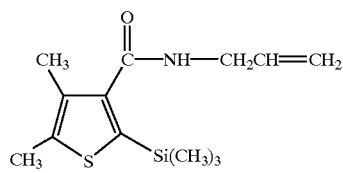

comprising:

(a) reacting a haloketone having the formula

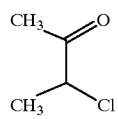

with NaSH in an aqueous/organic, two-phase solvent system;

(b) isolating the resulting mercaptoketone having the formula

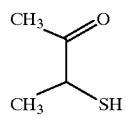

as a solution in the organic solvent;

(c) reacting the mercaptoketone of (b) with an acrylic compound having the formula

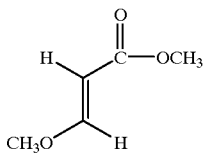

in the presence of an effective amount of a base as a catalyst;

(d) aromatizing by acid treatment the product of (c) with acid to produce a thiophene having the formula

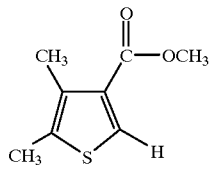

(e) hydrolyzing the carboxylic ester moiety of the thiophene of (d) to the corresponding Li salt;

(f) treating the Li salt product of (e) with a strong base and trimethylsilylchloride to replace the hydrogen atom on the thiophene ring with the trimethylsilyl moiety;

(g) converting the carboxylate substituent of the product of (f) to a N-propenyl amide moiety; and (h) recovering the 4,5-dimethyl-N-propenyl-2 (trimethylsilyl)-3-thiophene carboxamide produced in (g).

2. The process of claim 1, wherein the organic solution of the mercaptoketone of (b) is dried by azeotropic distillation or by contact with a desiccant before step (c).

3. The process of claim 1, wherein said base catalyst of (c) is an alkoxide.

4. The process of claim 3, wherein said alkoxide is selected from the group consisting of sodium methoxide, sodium t-amylate, potassium t-amylate, and potassium t-butoxide.

5. The process of claim 1, wherein said reaction of (c) is carried out in the presence of a hydrocarbon solvent.

6. The process of claim 1, wherein said reaction of (c) is carried out at a temperature between about 0–50° C.

7. The process of claim 1, wherein the amount of said base catalyst is about 0.025–0.2 equivalents relative to the amount of the mercaptoketone.

8. The process of claim 1, wherein step (d) comprises adding an effective amount of aqueous acid to the product of the reaction of (c) to convert any substituted tetrahydrothiophene to the equivalent substituted thiophene;

and wherein step (d) comprises the steps of:
(1) phase separating the organic portion of the mixture of aqueous acid and reaction product of (b);
(2) ev a porating any hydrocarbon solvent present to yield crude product thiophene; and
(3) distilling the crude thiophene product of (2) to yield a refined thiophene product.

* * * * *